United States Patent
Woerner et al.

(10) Patent No.: US 9,163,045 B2
(45) Date of Patent: Oct. 20, 2015

(54) PROCESS FOR PREPARING DIKETONATO-RHODIUM(I)-CARBONYL COMPLEXES

(71) Applicant: Umicore AG & CO. KG, Hanau (DE)

(72) Inventors: Eileen Woerner, Nidderau (DE); Timo Ebert, Kahl (DE); Ralf Karch, Kleinostheim (DE); Andreas Rivas-Nass, Schriesheim (DE); Angelino Doppiu, Seligenstadt (DE); Juergen Widmer, Rodenbach (DE)

(73) Assignee: UMICORE AG & CO. KG, Hanau-Wolfgang (DE)

( * ) Notice: Subject to any disclaimer, the term of this patent is extended or adjusted under 35 U.S.C. 154(b) by 0 days.

(21) Appl. No.: 14/397,131

(22) PCT Filed: Apr. 25, 2013

(86) PCT No.: PCT/EP2013/058628
§ 371 (c)(1),
(2) Date: Oct. 24, 2014

(87) PCT Pub. No.: WO2013/160401
PCT Pub. Date: Oct. 31, 2013

(65) Prior Publication Data
US 2015/0141685 A1   May 21, 2015

(51) Int. Cl.
*C07F 15/00* (2006.01)
*C07C 45/50* (2006.01)

(52) U.S. Cl.
CPC ............... *C07F 15/008* (2013.01); *C07C 45/50* (2013.01); *C07F 15/0073* (2013.01)

(58) Field of Classification Search
CPC .............................. C07F 15/0073; C07C 45/50
USPC ............................................. 556/16; 568/454
See application file for complete search history.

(56) References Cited

FOREIGN PATENT DOCUMENTS

| | | | |
|---|---|---|---|
| CN | 102093432 A | * | 6/2011 |
| DE | 1 806 293 | | 10/1968 |
| EP | 0 068 480 A1 | | 1/1983 |
| EP | 0 257 967 A2 | | 3/1988 |
| EP | 0 429 963 A1 | | 6/1991 |
| GB | 1243 190 | | 8/1971 |
| GB | 1243190 A | * | 8/1971 |
| GB | 1 284 615 | | 8/1972 |
| GB | 2 075 857 | | 11/1981 |

OTHER PUBLICATIONS

Du et al., Applied Catalysis B: Enviromental, vol. 84, pp. 490-496 (2008).*
Freeman et al., Inorganic Chemistry, vol. 25, No, 10, pp. 1556-1560 (1986).*
Serron et al., Organometallics, vol. 17, No. 4, pp. 534-539 (1998).*
A.C. Jesse, M.A.M. Meester, D.J. Stufkens and K. Vrieze, Vibrational and NMR Spectroscopic Studies on (acac)M(substituted olefin)$_2$ (M=Rh(I), Ir(I)) 1978; pp. 129-136.
Marie E. Krafft and Lawrence J, Wilson, Synthesis and Characterization of Rhodium(I) Amino-Olefin Complexes., Organometallics 1988; pp. 2528-2534.
R.Grigg and J.L, Jackson, Rhodium Complexes of Some Cyclo-Olefins; Tetrahedron, vol. 29, 1973; pp. 3903-3907.
R. Grigg and J.L. Jackson, Rhodium Complexes of Cycol-Olefins, Tetrahedon letters No. 40, pp. 3493-3496, 1970.
Alexandr Jegorov, Oxidative Addition of Diphenylphosphinoacetic Acid to Rhodium: Crystal Structures of the Intermediate, [RhCl(H)(Ph$_2$PCH$_2$CO$_2$—OP)(Ph$_2$PCH$_2$CO$_2$H-P)$_2$]and of the Final Product, [Rh(Ph$_2$PCH$_2$CO$_2$—OP)$_3$], J.Chem. Soc. Dalton Trans. 1990; pp. 3259-3263.
Brink, et al., (Acetylacetonato) carbonyl(dicyclohexylphenylphosphine) rhodium(I), Metal-Organic Papers, 2007, pp. m48-m50.
Ju. S. Varshaysky, et al. Dimethylformamide Carbonylation of Platinum Group Metals Under Mild Homogeneous Conditions: Reactions of Carbonyl-Containing Complexes. J.Organometal. Chem, 31(1971) pp. 119-122.
Fiavio Bonati and Renato Ugo, Rhodium(I) and Indium(I) Carbonyl Derivatives of Some Schiff Bases of Acetylacetone, J.Organometal, Chem, 7 (1967) pp. 167-180.
Brian T. Heaton, et al. Rhodium(I) complexes containing the enolate of N-acetyl-3-butanoyltetramic acid (Habta) and the crystal structure of [Rh(abta){P(OPh)$_3$}$_2$], J. Chem. Soc., 1996, pp. 1701-1706.
S,H.H. Chaston, et al. Chemistry of the Metal Carbonyls. Part LIV. Synthesis of Rhodium and Iridium Carbonyls, J.Chem.Soc (A), 1969, pp. 500-502.
P.G.I Rasmussen, et al. Complexes of the New Ligand Tetracyasnobiimidazole. J.Am. Chem. Soc. 1982, 104, pp. 6155-6156.

(Continued)

*Primary Examiner* — Porfirio Nazario Gonzalez
(74) *Attorney, Agent, or Firm* — Smith, Gambrell & Russell, LLP

(57) ABSTRACT

The invention relates to a process for preparing diketonato-rhodium(I)-carbonyl complexes, especially diketonato-rhodium(I)-triorganophosphine-carbonyl complexes, for example Rh(CO)(PPh$_3$)acac. The process according to the invention is a "one-pot synthesis" and features a process procedure without intermediate isolation stages. After introduction of an Rh(III) halide precursor into a solvent and sparging with carbon monoxide (CO), a diketo compound of the R'—C(=O)—CH$_2$—C(=O)—R" type and a base are added, forming the intermediate compound diketonato-Rh(CO)$_2$. After addition of a triorganophosphine of the PR$_3$ type, the reaction mixture is heated and the diketonatocarbonyltriorganophosphine-rhodium(I) complex is removed. The process enables a rapid operation and a high yield. The complex Rh(CO)(PPh$_3$)acac prepared in accordance with the invention, because of its purity, is particularly suitable as a catalyst or precatalyst for homogeneous catalysis, for example for hydroformylation reactions.

25 Claims, No Drawings

(56) References Cited

OTHER PUBLICATIONS

A.M. Trzeciak, et al. Infrared and NMR, $^1$H, 19F, 31P Studies of Rh(I) Complexes of the Formula: [Rh(β-diketone)CO)$_x$(P)$_y$](x=0,1,2;x+Y=2;P=PPh$_3$ or P(OPh)$_3$), Inorganica Chimica Acta (1985) pp. 15-20.

Stefanus Otto, et al., Electron density manipulation in rhodium(I) phosphine complexes: structure of acetylacetonatocarbonylferrocenyl-diphenylphosphinerhodium(I), Polyhedron, 1998, pp. 2447-2453.

J. Antonio Abad, et al. Chemistry of Di -and Tri-metal Complexes with Bridging Carbene or Carbyne Ligands, Part 20. $^1$Complexation of Carbon-Metal Triple Bonds with Low-valent Metal Species; Crystal Structures of the Bimetal Complexes [CrW(μ—CC$_6$H$_4$Me—4)(CO)$_4$(n—C$_5$H$_5$)(n—C$_5$Me$_6$)]and [CoW(μ—CC6H4Me—4)(CO)3(n-C5Me$_5$)], J. Chem. Soc Dalton Trans. 1983 pages 2075-2081.

Vincent Cèsar, et al. Cationic and Neutral Rhodium(I) Oxazolinylcarbene Complexes, Eur. J.Inorg.Chem, 2004 pp. 3436-3444.

R, Colton, et al. Carbonyl Halides of the Group VIII Transition Metals, Aust: J.Chem., 1970, 23, pp. 1351-1358.

R.B. King, et al. Alkylrhodium Tetracarbonyl Derivatives as Catalytic Intermediates in Homogeneous Hydroformylation Reactions. An Infrared Spectroscopic Study, American Chemical Society 1979, pp. 4893-4896.

Martin Capka, et al. Hydrogenation and hydrosilylation activity of homogeneous and immobilized dicarbonyl(2,4-pentanedionato) rhodium complexes, Journal of Molecular Catalysis, 74 (1992) pp. 335-344.

J.G. Leipoldt, et al. The Crystal Structure of Acetylacetonatocarbonyltri-phenylphosphinerhodium(I), Inorganica Chimica Acta., 26 (1978), pp. L35-L37.

W. Sheng-guo et al. X. Xiao-dong, S. Guo-rong, Synthesis and Characterization of Acetylacetonatocarbonyltripbenylphoshinerhodium(I), Precious Metals, 2005, 26, [Publikation in Chinesisch] pp. 43-51 (English translation provided herewith).

F. Bonati and G. Wilkinson, Dicarbonyl-β-diketonato-and Related Complexes of Rhodium(I). J. Chem. Soc., 1964 pp. 3156-3160.

Yu, S. Varshaysky, at al., Mixed Carbonyl-Cyclooctene Complexes of Rhodium(I). *cis*-Cyclooctene as Ligand Organomet. Chem., 77(1974) 107-115.

W.J. Tic, J. Szymanowski, The synthesis of a rhodium catalyst for the hydro-formylation of propylene, Przemysl Cherniczny 2002, 81(6), pp. 386-390 [Publikation in Polnisch] (English translation provided herewith).

Nifant'Yev E. Ye., Shikovets T.A., Gavrilov K.I., Teleshev A.T. Intermolecular Redistribution Of Ligands in the System [Rh(CO)$_2$Cl]$_2$—[RhAcac(CO)L] pp. 854-855 (English translation provided herewith).

W.Hieber et al. Das Rhodium im System der Metallcarbonyle-Z. Anorg.u. Allgem. Chem 1943, pp. 96-113.

Junming Du et al.—The Influence of precursors on Rh/SBA-15 catalysts for N$_2$0 decomposition-Applied Catalysis B: Environment Elsevier, vol. 84 (2008) pp. 490-496.

Ewa Mieczynska et al.—Hydroformylation and isomerization of hex-1-ene catalyzed by [Rh(acac)(CO)(PPh$_3$)]: effect of modifying ligands, Journal of Molecular Catalysis, 73 (1992) pp. 1-8.

J. Powell et al.—Transition Metal-Carbon Bonds. Part XIII Di-u-chlorodicarbonyldi-ethyiene-dirhodium-I, Journals of the Chemical Society A—Jan. 1, 1968—pp. 211-212.

\* cited by examiner

PROCESS FOR PREPARING DIKETONATO-RHODIUM(I)-CARBONYL COMPLEXES

The invention relates to a process for preparing diketonato-rhodium(I)-carbonyl complexes, in particular diketonatocarbonyltriorganophosphinerhodium(I) complexes such as acetylacetonatocarbonyltriphenylphosphinerhodium(I) Rh(CO)(PPh$_3$)acac, hereinafter also referred to as "Ropac".

The process of the invention is distinguished by an improved, single-stage process procedure which dispenses with any intermediate isolation or intermediate purification stages (known as "one-pot synthesis"). In the present application, a process which may comprise a plurality of process steps but is carried out in a single vessel without intermediate isolation steps is also referred to as "single-stage", which comes within the meaning of the above-described one-pot synthesis.

As a result of the single-stage process, the present invention makes possible a quick process procedure in the preparation of the diketonatocarbonyltriorganophosphinerhodium(I) complexes according to the invention. The use of inexpensive and environmentally friendly solvents makes it possible to carry out the process economically on an industrial scale. Furthermore, good yields are achieved.

The diketonatocarbonyltriorganophosphinerhodium(I) complexes prepared are particularly useful as catalysts or precatalysts for homogeneous catalysis, for example for hydroformylation reactions.

PRIOR ART

Numerous multistage processes for preparing diketonatocarbonyltriorganophosphinerhodium(I) complexes are known in the prior art; these are all multistage in that intermediate products have to be isolated in a complicated manner. In general, Rh(CO)(PPh$_3$)acac is prepared by reacting the starting complex dicarbonylRh(I) acetylacetonate Rh(CO)$_2$(acac) with triphenylphosphine. Here, Rh(CO)$_2$(acac) is prepared from rhodium chloride hydrate, for example in dimethylformamide, with addition of acetylacetone, filtered and washed and subsequently reacted.

Leipoldt et al. and Sheng-guo et al. describe the preparation of Rh(CO)$_2$(acac) from RhCl$_3$ hydrate in dimethylformamide/acetylacetone by precipitation after addition of water, isolation and washing of the compound prepared with petroleum ether (see: J. G. Leipoldt, S. S. Basson, L. D. C. Bok and T. I. A. Gerber, *Inorganica Chim Acts.*, 1978, 26, L35-L37; and: W. Sheng-guo, X. Xiao-dong, S. Guo-rong, Z. Ying-kui, *Precious Metals*, 2005, 26, 43-51 [publication in Chinese]).

In a separate reaction step, Leipoldt et al. convert the resulting rhodium-carbonyl complex in benzene with addition of triphenylphosphine (hereinafter referred to as PPh$_3$ for short) into Rh(CO)(PPh$_3$)acac. Precise details in respect of temperature and reaction times are not disclosed; it is merely stated that the benzene is removed after the formation of carbon monoxide resulting from the reaction has stopped. The preparation of Rh(CO)(PPh$_3$)acac is consequently a multistage synthesis. Details regarding the precise yield are absent.

Sheng-guo et al. also subsequently react the Rh(CO)$_2$(acac) obtained in a separate reaction step with addition of PPh$_3$ in toluene for a reaction time of one hour to give Rh(CO)(PPh$_3$)acac, but no precise details regarding the reaction temperatures are present. A yield of 91% is achieved by means of the multistage process described.

Bonati and Wilkinson describe, in their synthesis, firstly the preparation of Rh(CO)$_2$(acac) from tetracarbonyldichlorodirhodium [Rh(CO)$_2$Cl]$_2$ with addition of barium carbonate and acetylacetone in petroleum by stirring for about one week. The (CO)$_2$Rh(acac) complex obtained is, after removal of the solvent, reacted in a separate process stage in benzene with addition of PPh$_3$ to form Rh(CO)(PPh$_3$)acac. Bonati and Wilkinson, too, therefore envisage a multistage process (see: F. Bonati, G. Wilkinson, *J. Chem. Soc.*, 1964, 3156-3160).

Varshavsky et al., too, describe a preparative process starting out from [Rh(CO)$_2$Cl]$_2$. Rh(CO)(PPh$_3$)acac is prepared from rhodium-carbonyl complexes with addition of PPh$_3$ in hexane in a separate process stage (see: Y. S. Varshavsky, T. G. Cherkasova, N. A. Buzina, V. A. Kormer, *J. Organomet. Chem.*, 1974, 77, 107-115).

Tic and Szymanowski describe a three-stage process for preparing Rh(CO)(PPh$_3$)acac. RhCl$_3$ hydrate is firstly reacted with carbon monoxide at from 70 to 75° C. for from 0.5 to 3.5 hours. In a second process step, barium carbonate and acetylacetone are added at temperatures of from 45 to 60° C. and reacted for from 0.25 to 1.5 hours. Remaining barium carbonate and barium chloride formed are subsequently removed by filtration and the solvent is subsequently removed by distillation, making the process time-consuming. The crystals of the intermediate Rh(CO)$_2$(acac) obtained in this way are dried. In a subsequent process step, Rh(CO)(PPh$_3$)acac is prepared by addition of PPh$_3$ in hexane at temperatures of 50° C. over a period of 0.5 hour. (see: W. J. Tic, J. Szymanowski, *Przemysl Chemiczny* 2002, 81(6), 386-390 [publication in Polish]).

It is therefore an object of the present invention to provide a process which allows inexpensive, single-stage preparation of diketonatocarbonyltriorganophosphinerhodium(I) complexes, in particular Rh(CO)(PPh$_3$)acac ("Ropac"), on an industrial scale. The process should additionally make it possible to prepare the rhodium-carbonyl complex in a high yield and with high purity.

The object of the present invention is achieved by the subject matter of the accompanying claims. The achievement of the object according to the invention comprises provision of a single-stage process for preparing diketonatocarbonyltriorganophosphinerhodium(I) complexes, in particular Rh(CO)(PPh$_3$)acac, which is, as a result of the chemicals used, the process conditions and the high yields which can be achieved, also both environmentally friendly and economical.

As mentioned above, a single-stage preparative process comprises, for the purposes of the present invention, the preparation of the diketonatocarbonyltriorganophosphinerhodium(I) complexes without any isolation of intermediates. The present invention therefore describes a process in which the target product is prepared in-situ from the starting materials in one reactor without costly and time-consuming intermediate isolations or intermediate purifications (hereinafter referred to as "one-pot synthesis").

The process of the invention allows simple isolation of the diketonatocarbonyltriorganophosphinerhodium(I) complexes since process conditions in which the target compounds are obtained directly from the reaction mixture are selected in a targeted manner. According to the invention, this comprises formation of a suspension containing, as a precipitate, compounds which can be separated off. Time-consuming and costly isolation, for example by means of separation, concentration or by means of other processes, is therefore not necessary.

The present invention provides a process for preparing the diketonatocarbonyltriorganophosphinerhodium(I) compound having the general formula (I)

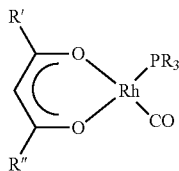

(I)

where
the radicals R are $C_1$-$C_{10}$-alkyl, $C_5$-$C_{10}$-cycloalkyl, $C_6$-$C_{12}$-aryl, $C_4$-$C_{12}$-heteroaryl radicals and
R' and R" are each, independent of one another, a $C_1$-$C_5$-alkyl, $C_5$-$C_{10}$-cycloalkyl, $C_6$-$C_{12}$-aryl radical,
where R, R' and R" may optionally be substituted,
which comprises the following reaction steps:
(a) introduction of an Rh(III) halide precursor into a solvent,
(b) treatment with carbon monoxide (CO) gas,
(c) addition of a diketone of the type R'—C(=O)—CH$_2$—C(=O)—R" and a base, forming the intermediate (diketonato)Rh(CO)$_2$,
(d) addition of a triorganophosphine of the type PR$_3$,
(e) heating of the reaction mixture and isolation of the diketonatocarbonyltriorganophosphinerhodium(I) complex of the formula (I).

In a preferred embodiment of the process, the diketonatocarbonyltriorganophosphinerhodium(I) complex Rh(CO)(PPh$_3$)(acac) is prepared. In this case, the process of the invention can be described by the following idealized and illustrative reaction equations:

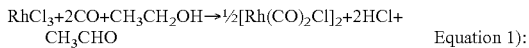

Equation 1):

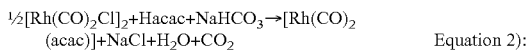

Equation 2):

Equation 3):

Equation 1) is, as mentioned above, an idealized reaction equation which serves merely for the purposes of the illustration. It is not known whether the reduction of Rh(III) is effected by CO or ethanol (or possibly by both).

However, the important thing in terms of the process of an invention is that the reaction proceeds from a soluble Rh(III) halide species in the presence of CO and in the presence of an organic solvent, preferably in the presence of an alcohol and particularly preferably in the presence of ethanol.

In the reaction equation 2), a diketo compound, preferably a 1,3-diketo compound of the type R'—C(=O)—CH$_2$—C(=O)—R", is added. For the purposes of the present invention, a 1,3-diketo compound is an organic molecule which has two ketone groups separated from one another by a methylene group. The radicals R' and R" can each be, independently of one another, a $C_1$-$C_5$-alkyl, $C_5$-$C_{10}$-cycloalkyl or $C_6$-$C_{12}$-aryl radical, where R' and R" may optionally be substituted. Preference is given to the radicals R' and R" each being, independently of one another, a $C_1$-$C_5$-alkyl, $C_5$-$C_{10}$-cycloalkyl or $C_6$-$C_{12}$-aryl radical which is not substituted. Examples of suitable diketo compounds of the type R'—C(=O)—CH$_2$—C(=O)—R" are acetylacetone (CH$_3$—CO—CH$_2$—CO—CH$_3$, R'=R"=methyl), 2,4-hexanedione (R'=methyl, R"=ethyl, trivial name propionylacetone), 2,2-dimethyl-3,5-hexanedion (R'=methyl, R"=t-butyl), 2,4-heptanedione (R'=methyl, R"=propyl; trivial name butanoylacetone), 6-methyl-2,4-heptanedione (R'=methyl, R"=iso-propyl, trivial name isovalerylacetone) and 1,3-diphenyl-1,3-propanedione (R'=R"=phenyl). The particularly preferred 1,3-diketo compound is acetylacetone.

During the course of the reaction, the 1,3-diketo compound is converted into the anionic diketonato compound and is bound as a bidentate, singly negatively charged ligand to the Rh central atom, cf. reaction equation 2).

In order to scavenge liberated HCl which is still present and to ensure a complete reaction, a base (for example NaHCO$_3$) is added in excess. An advantage of the use of carbonates or hydrogencarbonates as base is the ease of removal of reaction products (CO$_2$) via the gas phase and thus a shift in the equilibrium in the direction of the product. The poor solubility of the reaction products NaCl and of the (diketonato)(CO)$_2$Rh in the solvent selected also contributes to this. A suspension is obtained as a result.

In equation 3), a triorganophosphorus compound is added to the reaction mixture. Here, one CO ligand is replaced. It is possible to use triorganophosphines of the type PR$_3$, in particular trialkylphosphines or triarylphosphines.

In the triorganophosphine of the type PR$_3$, the radicals R are generally $C_1$-$C_{10}$-alkyl, $C_5$-$C_{10}$-cycloalkyl, $C_6$-$C_{12}$-aryl or $C_4$-$C_{12}$-heteroaryl radicals which may optionally be substituted. Examples are tributylphosphine, triisobutylphosphine, tricyclopentylphosphine, tricyclohexylphosphine or tri(o-tolyl)-phosphine. Examples of triorganophosphines having heteroaryl radicals are tri(2-furyl)phosphine or diphenyl(2-pyridyl)-phosphine.

As radicals R, preference is given to $C_1$-$C_{10}$-alkyl, $C_5$-$C_{10}$-cycloalkyl or $C_6$-$C_{12}$-aryl radicals. In a particularly preferred embodiment, the triorganophosphine is triphenylphosphine (PPh$_3$).

The individual reaction steps a) to e) of the process of the invention are described in more detail below.

Reaction Step a)

Introduction of an at least partially soluble Rh(III) halide precursor into a solvent As Rh halide precursor, use is generally made of rhodium (III) chloride in the form of a solution or a soluble solid (e.g. RhCl$_3$xH$_2$O), preferably in the form of a ready-to-use aqueous rhodium(II) chloride solution. Water-containing rhodium (III) chloride solutions which have a rhodium content of <30% by weight, as are commercially available and are produced, for example, by dissolving rhodium metal in the presence of concentrated hydrochloric acid and chlorine gas, are typically used. However, suitable rhodium(III) chloride solutions can also be branched off from process streams of noble metal recycling or industrial noble metal chemistry. In addition, the use of a rhodium(III) chloride solution has the advantage over the customarily used solid RhCl$_3$ hydrate of cheaper and quicker processing, since preceding evaporation, isolation of RhC$_3$ hydrate and analysis (to determine the amount of starting material) are dispensed with. Ready-to-use Rh(III) chloride solution as starting material is therefore quicker to obtain and easier to handle.

The Rh(III) precursor is introduced into a solvent, preferably into an organic solvent. If the Rh(III) precursor is present as an aqueous rhodium(III) chloride solution, it is mixed with the solvent. If the Rh(III) precursor is present as a solid material, for example RhCl$_3$ hydrate, it is dissolved in the solvent.

The solvent is preferably an organic solvent, especially a low aliphatic alcohol, such as methanol, ethanol or isopropanol. These alcohols can optionally be mixed with water. In a preferred embodiment, the solvent comprises ethanol. In a further preferred embodiment, the diketo compound itself can be used as solvent, optionally in a mixture with water.

The use of alcohols such as ethanol makes it possible to use a uniform solvent throughout the total process, i.e. for the preparation of $[(CO)_2RhCl]_2$ (equation (1)), also for (diketonato)$Rh(CO)_2$ (equation (2)) and also later for the preparation of (diketonato)($PR_3$)Rh(CO) (equation (3)). Removal of solvent or a change of solvent is therefore not necessary. This results in an economically and ecologically advantageous process.

Preferred solvents for the process of the invention are in principle those in which the Rh(III) precursor and the dicarbonyl product $[(CO)_2RhCl]_2$ dissolve readily while the solubility of the intermediate (diketonato)$(CO)_2Rh$ and in particular of the target product (diketonato)($PR_3$)Rh(CO) is poorer, so that these in each case precipitate from the reaction mixture and the target product can be isolated directly by filtration without any complicated concentration steps or solvent replacement. Furthermore, the triorganophosphine of the type $PR_3$, which is used, preferably triphenylphosphine ($PPh_3$), should also be readily soluble in this solvent.

The use of alcohols such as ethanol also allow an inexpensive and more environmentally friendly preparation compared to the toxic solvents such as dimethyl formamide (DMF) which are usually used for this process in the first substep of preparation of (diketonato)$Rh(CO)_2$.

Reaction Step b)

Treatment with Carbon Monoxide (CO) Gas

The solution obtained in reaction step a) is subsequently admixed with carbon monoxide (CO) to produce the carbonyl compound $[Rh(CO)_2Cl]_2$. This results in a clear, yellow solution of dicarbonyl rhodium(I) chloride dimer. In a particular embodiment, the gas treatment step can be carried out in the presence of the diketo compound (i.e. reaction step c) can be carried out before step b)).

The treatment with CO gas is carried out at elevated reaction temperatures in the range from 25° C. to 80° C. The reaction temperatures are preferably selected in the range from 50° C. to 70° C.

In a preferred form, the reaction proceeds without use of a pressure atmosphere. However, carrying out the reaction under a slightly subatmospheric pressure is likewise possible.

The gas treatment time depends on the temperature and pressure parameters selected and is typically in the range from 2 to 24 hours, preferably from 2 to 16 hours, in order to achieve complete reaction. Intensive dispersion of the CO in the solution should be ensured during the CO gas treatment. The fine dispersion of the CO in the solution can be ensured by rapid stirring during introduction; as an alternative, it is possible to use sparging stirrers or gas distributors.

Reaction Step c)

Addition of the diketo compound (preferably acetylacetone) and a base, forming the intermediate (diketonato)Rh$(CO)_2$ The reaction mixture obtained in step b) is, without intermediate isolation of the Intermediate $[Rh(CO)_2Cl]_2$ obtained in-situ, cooled to temperatures below 40° C., preferably below 35° C. The diketo compound and a base are subsequently added. For the purposes of the invention, a base is a compound which can increase or set the pH of an aqueous solution to pH a 7, according to the invention preferably to a pH in the range from pH 7 to 10, more preferably to pH 7 to 8.

According to the invention, preference is given to adding first the diketo compound and subsequently the base.

The base is generally selected from the group consisting of alkali metal carbonates, alkaline earth metal carbonates, alkali metal hydrogencarbonates, alkaline earth metal hydrogencarbonates, alkali metal diketonates, alkaline earth metal diketonates and mixtures and combinations thereof. Examples of suitable inorganic bases are $NaHCO_3$, $Na_2CO_3$, $K_2CO_3$, $CaCO_3$ and $BaCO_3$. Examples of suitable organic bases are alkali metal or alkaline earth metal diketonates such as Na(acac) and Ca(acac)$_2$. In this case, use is ideally made of the diketo compound which is also present as diketonate ligand in the target product. The base which is preferred according to the invention is $NaHCO_3$.

When commercial rhodium(III) chloride solution is used, the addition of from 2 to 12 molar equivalents of base (e.g. $NaHCO_3$) (based on the amount of Rh used), is advantageous; preference is given to using from about 5 to 10 molar equivalents of base (based on the amount of Rh used) to effect sufficient neutralization of the acidic components present in the rhodium chloride solution.

It has been found that the diketo compound should be added in an amount of at least 2 molar equivalents, preferably in an amount of from 5 to 12 molar equivalents and particularly preferably in an amount of from 8 to 12 molar equivalents (based on the amount of Rh used). The reaction mixture can optionally be additionally stirred at temperatures below 40° C. after addition of the base. The intermediate (diketonato)$Rh(CO)_2$, in particular $Rh(CO)_2$(acac) generally precipitates in this reaction, giving a reaction mixture in which the intermediate (diketonato)$Rh(CO)_2$ is present in suspended form (i.e. in a suspension).

Reaction Step d)

Addition of a Triorganophosphine to the Reaction Mixture

The intermediate (Diketonato)$Rh(CO)_2$ produced by the above-described process is converted further into the target product (diketonato)Rh(CO)($PR_3$), which is generally obtained in the form of a yellow solid. It has surprisingly been found that intermediate isolation of (diketonato)$Rh(CO)_2$ is not necessary for the preparation of (diketonato)Rh(CO)($PR_3$). According to the invention, the preparation of (diketonato)Rh(CO)($PR_3$)acac is therefore carried out directly from the reaction mixture obtained in reaction step c) by addition of a triorganophosphorus compound (preferably triphenylphosphine, $PPh_3$).

It has been found that this reaction proceeds from a suspension to form a further suspension. (Diketonato)$Rh(CO)_2$ has a small residual solubility in the solvent selected. The small amount of dissolved material reacts with the (partially) dissolved phosphine $PR_3$; this results in precipitation of the end product from the reaction mixture, and CO is additionally liberated. In general, the solubility of the end product (diketonato)($PR_3$)(CO)Rh in alcohols is lower than that of the intermediate (diketonato)$(CO)_2Rh$.

The triorganophosphine of the type $PR_3$ is added in a proportion of from 0.98 to 1.08 molar equivalents, based on Rh. According to the invention, preference is given to adding from 1.01 to 1.03 molar equivalents of phosphine since this ensures a high yield of pure target compound. Furthermore, the target compound is obtained in higher purity as a result of this measure, since only very small amounts of chlorine-containing by-product are formed.

According to the invention, the triorganophosphine is preferably added in pure form, in the case of $PPh_3$ as a solid. The addition of dissolved phosphine is likewise possible. In this case, organic solvents in which the triorganophosphine dissolves are used. Examples of such organic solvents are aliphatic or aromatic hydrocarbons, e.g. n-hexane, petroleum ether or toluene. The addition is generally carried out at a temperature of above 15° C. and up to 40° C., with the reaction mixture generally being stirred.

Reaction Step e)
Heating of the Reaction Mixture, Subsequently Cooling and Isolation of the Rh(I) Target Product After addition of the triorganophosphine, the reaction mixture is heated under reflux ("refluxed"), with, depending on the solvent or solvent mixture used, temperatures in the range from 50 to 120° C. being set. The maximum temperature to which the mixture is heated depends on the solvent or solvent mixture used. The refluxing time for complete reaction should generally be from 1 to 20 hours, preferably from 2 to 16 hours. This reaction step is not necessary in all cases, but makes it possible to isolate a very pure product.

After (optional) cooling, the compound can be separated off from the reaction mixture, preferably by filtration. Washing is generally carried out using a water-miscible organic solvent and/or deionized water (DI water). The end product can be washed free of chloride by washing with DI water. To remove further impurities, aliphatic alcohols (preferably ethanol) are preferably used. The product is usually dried at temperatures in the range from 30 to 60° C., preferably in the range from 35 to 50° C. Drying is preferably carried out under reduced pressure, but can also be carried out under air or inert gas (argon, nitrogen, etc.).

When the conditions and steps of the above-described single-stage preparative process of the invention are adhered to, the target products of the type (diketonato)($PR_3$)(CO)Rh, in particular Rh(CO)($PPh_3$)acac can be obtained in high yield and purity. In the process of the invention, the yields are above 93%, preferably above 95%. Here, the yield is based on the rhodium contents present, i.e. the yield "OMB" ("on metal basis"). Overall, the process time of conventional multistage processes for preparing Rh(CO)($PPh_3$)acac is reduced by more than half by means of the process of the present invention. This leads to a high economical importance of the process.

Owing to the good yields and the high purity of the end product and also owing to the cost-efficient and environmentally friendly selection of parameters in the process, it is predestined for the industrial scale.

The rhodium-carbonyl complex Rh(CO)($PPh_3$)acac ("Ropac") prepared by the one-pot process of the invention is, owing to the excellent purity and the resulting high catalytic activity, particularly suitable as catalyst or precatalyst, preferably in hydroformylation reactions, for example for the conversion of alkenes. The alcohols prepared in this reaction have a variety of uses in industry.

Analytical Data

The Rh compounds of the type (diketonato)($PR_3$)(CO)Rh prepared according to the invention, in particular Rh(CO)($PPh_3$)acac ("Ropac"), have a low content of chlorine (total chlorine content, including free and bound chloride determined by the Wickboldt method). The proportion of chloridic impurities is generally <0.1% by weight (1000 ppm), preferably <0.03% (300 ppm), determined by means of a chlorine analyzer (from Analytik Jena). These low chlorine values ensure the good catalytic activity of the compound prepared according to the invention.

The proportion of the compound Rh(CO)($PPh_3$)$_2$Cl, in particular, can be determined (e.g. by means of signal splitting at approximately 30 ppm) in the $^{31}$P-NMR spectrum of the product Rh(CO)($PPh_3$)acac ("Ropac"). In general, the percentage by area of the peak of Rh(CO)($PPh_3$)$_2$Cl in the $^{31}$P-NMR spectrum based on the proportion by area of the peak of Rh(CO)($PPh_3$)acac is less than 5%, preferably less than 1%, particularly preferably less than 0.3% (measured in $CDCl_3$ and based on the area of the peaks of the two compounds in the $^{31}$P-NMR spectrum). The compound Rh(CO)($PPh_3$)$_2$Cl has only a low catalytic activity and should therefore be present in very small amounts in the Rh(CO)($PPh_3$)acac product.

The process of the invention is illustrated by the following examples.

EXAMPLE 1

1.6 kg of ethanol (technical grade) are placed in a 10 l double-wall reactor provided with stirrer, baffle, reflux condenser and a gas inlet tube equipped with a glass frit and stirred. While continuing to stir, 200.0 g of rhodium (1.94 mol) in the form of rhodium(III) chloride solution (Rh(III) chloride solution, Umicore product No. 68.2565.2720; Rh content about 20% by weight) are added to the solution.

The stock vessel for the rhodium chloride solution is rinsed a number of times with a total of 1.7 kg of ethanol and this is added to the solution in the reactor. The reactor is brought to 25° C. and carbon monoxide (CO: grade 2.0, from Linde) is passed through the reaction mixture via the gas inlet tube at a gas flow of about 65 l/h. The internal reactor temperature is quickly brought to about 60° C. After the gas treatment temperature has reached 60° C., the gas treatment is continued for about 7 h. The reactor is then quickly cooled to an internal temperature of 30° C. and the supply of gas is subsequently stopped. While stirring, 2.14 kg of acetylacetone (synthesis grade) are added to the reaction mixture. 1.63 kg of sodium hydrogencarbonate (high-purity) are introduced via a solids funnel over a period of 30 minutes. This results in the reaction mixture foaming due to the liberation of carbon dioxide. After all the sodium hydrogencarbonate has been added, the mixture is stirred at 30° C. for a further 60 minutes. 515 g of triphenylphosphine (1.96 mol, min. 99.5%, Imhoff & Stahl) are added to the resulting suspension over a period of 20 minutes. This results in liberation of carbon monoxide. After stirring for about 30 minutes, the reaction mixture is heated under reflux at an internal temperature of about 74° C. for about 16 h. After cooling to room temperature, the suspension is filtered through a suitable glass frit. The filter cake is washed a number of times with a total of 0.8 kg of ethanol and subsequently washed free of chloride with a number of portions of DI water (Cl determination by means of the residual conductivity, and by precipitating testing using silver nitrate solution). After washing again with 0.8 kg of ethanol and 0.7 kg of petroleum ether (50/70), the filter cake is dried at 40° C. in a vacuum drying oven.

This gives about 953.5 g of yellow solid having a rhodium content of 20.76%. (Determination of the Rh content by ICP-OES after digestion with sulfuric acid and nitric acid). This corresponds to a rhodium-based yield of 99%. The total chlorine content is <0.03% (Wickboldt digestion).

The identity of the product ($PPh_3$)(CO)Rh(acac) is determined by $^{31}$P-NMR spectroscopy (in $CDCl_3$). This shows a doublet at about 50 ppm (signals at 49.5 and 51.1 ppm). The percentage by area of the peak of the by-product Rh(CO)($PPh_3$)$_2$Cl in the $^{31}$P-NMR spectrum based on the proportion by area of the peak of Rh(CO)($PPh_3$)acac is <1%.

Repetition of the batch with CO gas treatment for 16 h gives a rhodium-based yield of 99.7%, and a Cl content of <0.03%.

EXAMPLE 2

40.0 g of rhodium (0.39 mol) in the form of 101.9 g of Rh(III) chloride hydrate (Umicore product no. 68.2562.1138, 39.25% Rh content), 437 ml of acetylacetone (4.29 mol) and 431 ml of ethanol (technical grade) are placed in a 1 l double-wall reactor provided with reflux condenser, precision glass stirrer and gas inlet tube. The mixture is treated while stirring with a CO gas stream of 20 l/h and at the same time heated to 60° C. These conditions are maintained for 13 h, and the mixture is subsequently cooled to about 30° C. The CO gas treatment is stopped. 326.5 g of NaHCO$_3$ are subsequently introduced in small portions into the solution over a period of about 30 minutes. This results in liberation of CO$_2$. The mixture is stirred for one hour. 105.0 g (0.4 mol) of triphenylphosphine are subsequently dissolved in 400 ml of toluene and added while stirring vigorously to the reaction mixture over a period of 20 minutes. Immediately afterwards (without an intermediate stirring time), the reaction mixture is heated to reflux temperature (about 73° C.). After refluxing for 8 h, the mixture is cooled to 25° C. and the resulting solid is filtered off via a glass frit and washed free of chloride with 15 liters of DI water introduced a little at a time. The solid is subsequently dried to constant weight at 40° C. under reduced pressure. This gives 38.04 g of rhodium in the form of 182.0 g of (PPh$_3$)(CO)Rh(acac) having an Rh content of 20.9%, corresponding to a rhodium-based yield of 95.1%.

A total Cl content of <0.03% is obtained. The identity and purity of the (PPh$_3$)(CO)Rh(acac) product is confirmed by means of $^{31}$P-NMR spectroscopy (in CDCl$_3$).

The invention claimed is:

1. A process for preparing the diketonatocarbonyltriorganophosphinerhodium(I) complex having the formula (I)

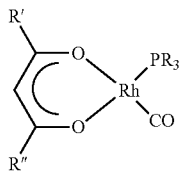

Formula (I)

where
R is C$_1$-C$_{10}$-alkyl, C$_5$-C$_{10}$-cycloalkyl, C$_6$-C$_{12}$-aryl, or C$_4$-C$_{12}$-heteroaryl and
R' and R" are each, independent of one another, a C$_1$-C$_5$-alkyl, C$_5$-C$_{10}$-cycloalkyl, or C$_6$-C$_{12}$-aryl, where R, R' and R" may optionally be substituted, which comprises the reaction steps:
(a) introduction of an Rh(III) halide precursor into a solvent,
(b) treatment with carbon monoxide (CO) gas,
(c) addition of a diketo compound of the type R'—C(=O)—CH$_2$—C(=O)—R" and a base, forming the intermediate (diketonato)Rh(CO)$_2$,
(d) addition of a triorganophosphine of the type PR$_3$,
(e) heating of the reaction mixture and isolation of the diketonatocarbonyltriorganophosphinerhodium(I) complex of the formula (I), and wherein the solvent of step (a) is used as a solvent throughout the process.

2. The process as claimed in claim 1, wherein acetylacetone, 2,4-hexanedione, 2,2-dimethyl-3,5-hexanedione, 2,4-heptanedione, 6-methyl-2,4-heptanedione or 1,3-diphenyl-1,3-propanedione, is used as diketo compound.

3. The process as claimed in claim 1, wherein a water-containing rhodium(III) chloride solution or solid Rh(III)Cl$_3$ hydrate is used as Rh(III) halide precursor in reaction step a).

4. The process as claimed in claim 1, wherein triphenylphosphine, tributylphosphine, triisobutylphosphine, tricyclopentylphosphine, tricyclohexylphosphine or tri(o-tolyl)-phosphine, is used as triorganophosphine of the type PR$_3$.

5. The process as claimed in claim 1, wherein an organic solvent, optionally in a mixture with water, is used as solvent in reaction step a).

6. The process as claimed in claim 1, wherein a lower aliphatic alcohol from the group consisting of methanol, ethanol and isopropanol and mixtures thereof is used as solvent in reaction step a).

7. The process as claimed in claim 1, wherein ethanol, optionally in a mixture with water, is used as solvent in reaction step a).

8. The process as claimed in claim 1, wherein the intermediate diketonatoRh(CO)$_2$ formed in step c) is present in suspension in the reaction mixture.

9. The process as claimed in claim 1, wherein the treatment with CO gas in reaction step b) is carried out at temperatures in the range from 25 to 80° C.

10. The process as claimed in claim 1, wherein the treatment with CO gas is carried out over a period of from 2 to 24 hours.

11. The process as claimed in claim 1, wherein an inorganic base selected from the group consisting of NaHCO$_3$, Na$_2$CO$_3$, K$_2$CO$_3$, CaCO$_3$ and BaCO$_3$ or an organic base selected from the group consisting of alkali metal or alkaline earth metal diketonates is used as base in reaction step c).

12. The process as claimed in claim 1, wherein the diketo compound is added in an amount of from 2 to 12 molar equivalents, per Mol of Rh in step c).

13. The process as claimed in claim 1, wherein the triorganophosphine is added in an amount of from 0.98 to 1.08 molar equivalents, per mol of Rh in reaction step d).

14. The process as claimed in claim 1, wherein the addition of the triorganophosphine in reaction step d) is carried out at a temperature of from 15 to 40° C.

15. The process as claimed in claim 1, wherein the heating in reaction step d) is carried out at temperatures in the range from 50 to 120° C. over a period of from 1 to 20 hours.

16. The process as claimed in claim 1, wherein the process is carried out in one stage without isolation of intermediates.

17. The process as claimed in claim 1, wherein the process is a one-pot synthesis.

18. The process as claimed in claim 1, which further comprises separation of the diketonatocarbonyltriorganophosphinerhodium(I) complex from the reaction mixture.

19. The process as claimed in claim 18, which further comprises washing of the diketonatocarbonyltriorganophosphinerhodium(I) complex using water-miscible organic solvents.

20. The process as claimed in claim 1, wherein the diketonatocarbonyltriorganophosphinerhodium(I) complex has the formula (II):

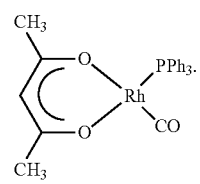

Formula (II)

21. Rh(CO)(PPh$_3$)acac obtained by the process as claimed in claim 20, wherein the content of the impurity Rh(CO)

(PPh$_3$)$_2$Cl is less than 5%, (measured in CDCl$_3$ and based on the area of the peaks of the two compounds in the $^{31}$P-NMR spectrum).

22. A homogeneous catalysis process comprising introducing the complex Rh(CO)(PPh$_3$)acac as claimed in claim 20 as a catalyst or a precatalyst for the homogeneous catalysis.

23. A process for preparing the diketonatocarbonyltriorganophosphinerhodium(I) complex having the formula (I)

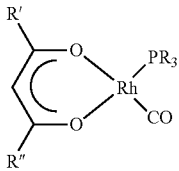

Formula (I)

where

R is C$_1$-C$_{10}$-alkyl, C$_5$-C$_{10}$-cycloalkyl, C$_6$-C$_{12}$-aryl, or C$_4$-C$_{12}$-heteroaryl and R' and R" are each, independent of one another, a C$_1$-C$_5$-alkyl, C$_5$-C$_{10}$-cycloalkyl, or C$_6$-C$_{12}$-aryl, where R, R' and R" may optionally be substituted, which comprises the reaction steps:

(a) introduction of an Rh(III) halide precursor into a solvent,
(b) treatment with carbon monoxide (CO) gas,
(c) addition of a diketo compound of the type R'—C(=O)—CH$_2$—C(=O)—R" and a base, forming the intermediate (diketonato)Rh(CO)$_2$,
(d) addition of a triorganophosphine of the type PR$_3$,
(e) heating of the reaction mixture and isolation of the diketonatocarbonyltriorganophosphinerhodium(I) complex of the formula (I), wherein the solvent is an alcohol, optionally mixed with water, and the alcohol is used as a uniform solvent throughout the entire process, and wherein the process is carried out in one stage without isolating intermediate reaction products.

24. A process for preparing the diketonatocarbonyltriorganophosphinerhodium(I) complex having the formula (I)

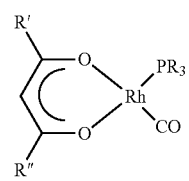

Formula (I)

where

R is C$_1$-C$_{10}$-alkyl, C$_5$-C$_{10}$-cycloalkyl, C$_6$-C$_{12}$-aryl, or C$_4$-C$_{12}$-heteroaryl and R' and R" are each, independent of one another, a C$_1$-C$_5$-alkyl, C$_5$-C$_{10}$-cycloalkyl, or C$_6$-C$_{12}$-aryl, Where R, R' and R" may optionally be substituted, which comprises the reaction steps:

(a) introduction of an Rh(III) halide precursor into a solvent, wherein the solvent is ethanol, optionally in a mixture with water,
(b) treatment with carbon monoxide (CO) gas,
(c) addition of a diketo compound of the type R'—C(=O)—CH$_2$—C(=O)—R" and a base, forming the intermediate (diketonato)Rh(CO)$_2$,
(d) addition of a triorganophosphine of the type PR$_3$,
(e) heating of the reaction mixture and isolation of the diketonatocarbonyltriorganophosphinerhodium(I) complex of the formula (I).

25. The process of claim 24, wherein the solvent is used as a uniform solvent throughout the process.

* * * * *